(12) United States Patent
Bates

(10) Patent No.: US 7,018,094 B1
(45) Date of Patent: Mar. 28, 2006

(54) MATERIAL ANALYSIS (75) Inventor: Daniel Bates, Coventry (GB)

(73) Assignee: Airbus UK Limited, Bristol (GB)

( * ) Notice: Subject to any disclaimer, the term of this patent is extended or adjusted under 35 U.S.C. 154(b) by 141 days.

(21) Appl. No.: 10/110,741

(22) PCT Filed: Oct. 13, 2000

(86) PCT No.: PCT/GB00/03938

§ 371 (c)(1),
(2), (4) Date: Aug. 15, 2002

(87) PCT Pub. No.: WO01/29545

PCT Pub. Date: Apr. 26, 2001

(30) Foreign Application Priority Data

Oct. 16, 1999 (GB) ................................. 9924425

(51) Int. Cl.
*G01J 5/02* (2006.01)
(52) U.S. Cl. ................... 374/121; 250/350; 250/341.6; 250/341.8
(58) Field of Classification Search ............... 374/4, 374/5, 7, 45, 44, 57, 120–121, 124, 129, 374/132; 250/341.6, 330, 332, 341.1, 341.2, 250/341.8
See application file for complete search history.

(56) References Cited

U.S. PATENT DOCUMENTS

| | | | | |
|---|---|---|---|---|
| 3,808,439 A | * | 4/1974 | Renius | 250/334 |
| 3,855,864 A | * | 12/1974 | Douglas | 73/355 R |
| 4,416,552 A | * | 11/1983 | Hessemer, Jr. et al. | 374/117 |
| 4,589,783 A | * | 5/1986 | Thomas et al. | 374/45 |
| 4,632,561 A | * | 12/1986 | Rosencwaig et al. | 356/432 |
| 4,686,222 A | | 8/1987 | Atkinson et al. | |
| 4,792,683 A | * | 12/1988 | Chang et al. | 250/341 |
| 4,797,555 A | * | 1/1989 | La Mar | 250/336.1 |
| 4,818,102 A | * | 4/1989 | Glenn | 356/43 |
| 4,818,118 A | * | 4/1989 | Bantel et al. | 374/7 |
| 4,872,762 A | * | 10/1989 | Koshihara et al. | 374/5 |
| 4,874,948 A | * | 10/1989 | Cielo et al. | 250/341.5 |
| 4,875,175 A | * | 10/1989 | Egee et al. | 364/551.01 |
| 4,950,897 A | * | 8/1990 | Mandelis et al. | 250/334 |
| 4,987,496 A | * | 1/1991 | Greivenkamp, Jr. | 358/448 |
| 5,068,799 A | * | 11/1991 | Jarrett, Jr. | 702/40 |
| 5,287,183 A | * | 2/1994 | Thomas et al. | 348/571 |
| 5,302,824 A | * | 4/1994 | Prager | 250/252.1 |
| 5,365,065 A | * | 11/1994 | Power | 250/330 |
| 5,374,122 A | * | 12/1994 | Devitt et al. | 374/45 |
| 5,568,978 A | * | 10/1996 | Johnson et al. | 374/161 |

(Continued)

FOREIGN PATENT DOCUMENTS

DE    35 20 777 A    11/1985

(Continued)

OTHER PUBLICATIONS

Front Flash Thermal Imaging Characterization of Continuous Fiber Ceramic Composites by Deemer et al. 1999.*

(Continued)

*Primary Examiner*—Gail Verbitsky
(74) *Attorney, Agent, or Firm*—Nixon & Vanderhye P.C.

(57) ABSTRACT

In thermography apparatus, a lamp 102 is modulated sinusoidally and a camera 106 captures thermal images at the modulated frequency, but delayed by an adjustable preset delay. A signal delay box 107 is connected between a sinusoidal modulation signal function generator 104 and the camera 106. The delay box introduces a delay to the function generator signal so that the thermal image is captured after a period of time, resulting in an enhanced image.

25 Claims, 5 Drawing Sheets

U.S. PATENT DOCUMENTS

| | | | |
|---|---|---|---|
| 5,654,977 A | 8/1997 | Morris | |
| 5,667,300 A * | 9/1997 | Mandelis et al. | 374/43 |
| 5,706,094 A * | 1/1998 | Maris | 356/432 |
| 5,711,603 A | 1/1998 | Ringermacher et al. | |
| 5,881,178 A * | 3/1999 | Tsykalov et al. | 382/260 |
| 6,000,844 A * | 12/1999 | Cramer et al. | 374/5 |
| 6,104,942 A | 8/2000 | Kruger | 600/407 |
| 6,234,016 B1 * | 5/2001 | Bonne et al. | 73/204.26 |
| 6,419,387 B1 * | 7/2002 | Legrandjacques et al. | 374/5 |
| 6,437,334 B1 * | 8/2002 | Thomas et al. | 250/341.6 |
| 6,488,405 B1 * | 12/2002 | Eppes et al. | 374/5 |
| 6,517,236 B1 * | 2/2003 | Sun et al. | 374/4 |
| 6,517,238 B1 * | 2/2003 | Sun et al. | 374/43 |
| 6,542,849 B1 * | 4/2003 | Sun | 702/172 |
| 6,595,685 B1 * | 7/2003 | Baba et al. | 374/161 |
| 6,690,016 B1 * | 2/2004 | Watkins et al. | 250/341.7 |
| 6,712,502 B1 * | 3/2004 | Zalameda et al. | 374/5 |
| 6,756,591 B1 * | 6/2004 | Lounis et al. | 250/316.1 |
| 6,860,350 B1 * | 3/2005 | Beuhler et al. | 180/167 |
| 2002/0018510 A1 * | 2/2002 | Murphy et al. | 374/45 |
| 2002/0126732 A1 * | 9/2002 | Shakouri et al. | 374/130 |
| 2002/0131476 A1 * | 9/2002 | Baba et al. | 374/161 |
| 2003/0202556 A1 * | 10/2003 | Taketoshi et al. | 374/45 |
| 2004/0050164 A1 * | 3/2004 | Bates | 73/587 |

FOREIGN PATENT DOCUMENTS

| | | |
|---|---|---|
| EP | 0 089 760 A | 9/1983 |
| EP | 0 919 802 A | 6/1999 |
| GB | 2 092 856 A | 8/1982 |
| GB | 2 235 604 A | 3/1991 |
| GB | 2 293 648 A | 4/1996 |
| JP | 02284087 A * | 11/1990 |

OTHER PUBLICATIONS

Phase Infrared Thermography by Maldague et al. 1996.*

NN85123037. Transient Thermal Imaging System. Dec. 1985.*

Roth D J et al; "Thermographic Imaging for High-Temperature Composite Materials- A Defect Detection Study"; Research in Nondestructive Evaluation, US, Springer Verlag, vol. 9, No. 3, 1997, pp. 147-169, XP000863003.

* cited by examiner

MATERIAL ANALYSIS

This application is the US national phase of international application PCT/GB00/03938 filed 13 Oct. 2000, which designated the US.

BACKGROUND OF THE INVENTION

1. Field of the Invention

The present invention relates to material analysis, and more particularly to material analysis using thermography.

2. Discussion of Prior Art

In known lock-in thermography material analysis a sample of a material to be analysed is positioned between a halogen lamp and an infra-red camera. The lamp is switched on and off by a sinusoidally modulated signal so that heat pulses are emitted towards the sample at a particular frequency, generating sinusoidal thermal waves inside the material. Reflections produced by defects and interfaces (normally boundaries between different materials) in the sample interfere with incoming waves transmitted by the lamp to produce a wave pattern at the surface of the material. The infra-red camera captures a thermal image of the wave pattern at the surface of the material.

U.S. Pat. No. 5,711,603, D. J. Roth et al., Res. Nondestr. Eval. 9 (1997) 147–169, EP0089760 A2 and GB2235604 A all disclose transient thermography techniques for nondestructive testing of material samples.

As the thermal images produced by the camera are captured at the same moment as when the halogen lamp is switched on, the system does not allow for thermal lag. Our studies have shown that it takes an appreciable amount of time for the heat pulses produced by the lamp to be transmitted from the surface of the sample facing the lamp through the thickness of the sample to the sample surface facing the camera. As a result of this, the camera is unable to accurately locate the sinusoidally varying heat pulses and so a poor signal-to-noise ratio is produced. Accordingly, the thermal images produced by the camera are of a "grainy" nature and therefore less useful for analysing imperfections in the material sample. It is often desirable to study imperfections at different depths within the sample. The limitations of the prior art lock-in thermography apparatus described above mean that it does not allow sufficient discrimination of imperfections at selected depths in the sample.

An aim of the present invention is to provide a system which produces improved thermal images for material analysis. One embodiment of the invention is intended to allow thermal images to be produced which represent selected points within the thickness of the material sample.

SUMMARY OF THE INVENTION

According to a first aspect of the present invention there is provided material analysis apparatus including:
 means for emitting a series of sinusoidally modulated heat pulses at a material sample;
 means for capturing a series of thermal images of said sample; and
 delay means for introducing a variable delay between said emission of each one of said series of sinusoidally modulated thermal pulses and capture of each of the respective series of thermal images.

In one embodiment the material sample is positioned between said heat pulse emitting means and said thermal imaging means. In a typical example, the heat pulses are emitted at a frequency approximately equal to 0.1 Hz and the delay is within a range of 0 seconds to 3 seconds.

In another embodiment the heat pulse emitting means and the thermal imaging means are positioned facing one surface of said material sample and the delay length is such that the thermal image is captured when energy resulting from the emitted heat pulse is reflected from a selected point within the thickness of the sample to the surface of the sample. The selected point may be represented by a distance measured from the surface of the sample.

Preferably, the thermal imaging means includes an infrared camera. The apparatus may further comprise means for storing digital data represent-ing said image captured by said camera.

Preferably, said heat pulse emitting means includes a halogen lamp and means for switching said halogen lamp on and off at a predetermined frequency. The infra-red camera is preferably configured to operate at a frequency of approximately 25 Hz such that approximately 25 thermal images are captured per one second and the halogen lamp is switched on and off at a frequency of approximately 0.1 Hz such that approximately 250 thermal images are captured in a period of approximately 10 seconds. The 250 thermal images captured are preferably used to produce 4 averaged images. Preferably, 5 said series of pulses are emitted and 5 said series of thermal images are captured such that 20 said averaged images are produced. The 20 averaged images may be used to produce a further averaged image. The delay means may include an operational amplifier circuit connected between said switching means and a personal computer connected to said thermal imaging means.

According to a second aspect of the present invention there is provided a method of analysing a material comprising steps of:
 emitting a series of sinusoidally modulated heat pulses towards a material sample, and
 capturing a series of thermal images of said sample, wherein a variable delay is introduced between said emission of each one of said series of sinusoidally modulated pulses and capture of each of the respective series of thermal images.

The heat pulses may be emitted at a frequency approximately equal to 0.1 Hz and the delay may be within a range of 0 seconds to 3 seconds.

The method may further include a step of selecting a point within the thickness of the sample, and calculating the delay length such that thermal images are captured when energy resulting from the emitted heat pulse is reflected from the selected point to the surface of the sample.

The series of thermal images may be captured at a frequency of approximately 25 Hz such that approximately 250 thermal images are captured in a period of approximately 10 seconds. The 250 thermal images are preferably used to produced four averaged images. Preferably, five said series of pulses are emitted and five said series of thermal images are captured such that 20 said averaged images are produced. The 20 averaged images may be used to produce a further averaged image.

BRIEF DESCRIPTION OF THE DRAWINGS

The invention may be performed in various ways, and, by way of example only, an embodiment thereof will now be described, reference being made to the accompanying drawings, in which.

DETAILED DISCUSSION OF EMBODIMENTS

Figure 1:
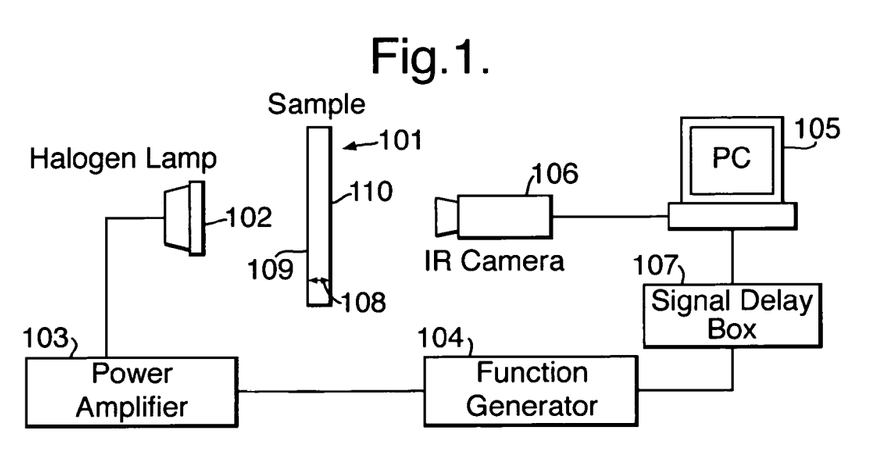
FIG. 1 illustrates schematically a particular embodiment of the present invention wherein a halogen lamp and an infra-red camera are located either side of a material sample.

In FIG. 1, a sample 101 of the material to be analysed is positioned with one surface 109 facing a halogen lamp 102. An opposite surface 110 of the sample 101 faces an infra-red camera 106. The thickness of the sample 101 between the two opposite surfaces 109 and 110 is indicated by arrows 108. Although in the example of FIG. 1 the thickness 108 of the sample material 101 is less than the length of the sample, in this specification the term "thickness" is intended to mean a distance between any two generally opposed surfaces of a material which is to be analysed.

The halogen lamp 102 is connected to a power amplifier 103 driven by a function generator 104 which in use switches the halogen lamp 102 on and off at a predetermined frequency provided by the sinusoidal function gen rator 104. The lamp 102 emits heat pulses in a direction mainly towards the surface 109 of the sample 101 adjacent to the lamp.

The function generator 104 is also connected via a signal delay box 107 and a personal computer (PC) 105 to the infra-red camera 106. The PC 105 is configured to activate the camera 106 when it receives the signal from function generator 104 via delay box 107. As the box 107 introduces a delay to the signal generated by component 104, the camera 106 captures a thermal image of the surface 110 of the sample 101 after the heat pulse has been emitted by lamp 102. The camera 106 produces digital data representing the thermal image which may be stored in a memory or external storage of the PC 105 for subsequent processing or display. The PC 105 normally uses a series of captured images produced during a specific period of time and processes them in order to produce a final image of enhanced quality. The image capturing may be synchronised with the modulation frequency and up to 250 Images may be captured within one cycle (i.e. switching of the lamp on and off) which are then averaged to provide 4 images. Thus, up to 4 signal values may be captured for every pixel of the image during a single cycle. A typical inspection may require 5 such cycles to be completed resulting in the production of 20 averaged thermal images. The image processing may involve summation of elements of the series of captured images and generating an "average" final value from the 20 averaged thermal images.

The signal delay box 107 utilises an operational amplifier circuit to introduce a variable time delay of up to one wavelength of the frequency of the sinusoidal signal generated by function generator 104. Typically a delay in a range of 0 seconds to 3 seconds would be introduced for a modulation frequency at least approximately equal to 0.1 Hz. The delay is of a length such that the infra-red camera 106 captures an image of the surface 110 of sample 101 at a time when energy resulting from a heat pulse most recently emitted by lamp 102 has had sufficient time to be transmitted at least partly through the thickness 108 of the sample. The calculation of the time delay may also take into account further user-defined factors, e.g. the type of material, the type of lamp used, etc. The signal delay box 107 includes means for varying the resulting delay.

This technique enables the camera and PC system to accurately locate the sinusoidal heat pulse from the halogen lamp which improves the signal to noise ratio which in turn minimises the effect of the grainy appearance of the images produced. The improved thermal image quality means that analysis results based on the images can be more reliable than using conventional lock-in thermography apparatus.

FIGS. 2 to 9 illustrate images taken of a 6 mm thick carbon fibre reinforced polymers (CFRP) plate with three polytetrafluoroethylene (PTFE) inclusions at various depths. The shaded images shown on the left hand side of the Figures represent the temperature variation over the surface of the sample facing the camera. Darker shading corresponds to lower temperatures, which allows inclusions in the sample to be identified, as their presence disrupts the flow of the heat pulse energy through the sample to the surface.

The images of FIGS. 2 to 9 were taken with increasing amounts of signal delay. An eight position delay box was constructed for the experimental trials providing a maximum of 3.0 seconds delay time with a modulation frequency of 0.1 Hz. The preferred embodiment may function with frequencies of up to 0.5 Hz. Generally, the lower the frequency, the more time the energy resulting from each heat pulse has to travel through the thickness of the sample before the next pulse is emitted.

Figure 2:
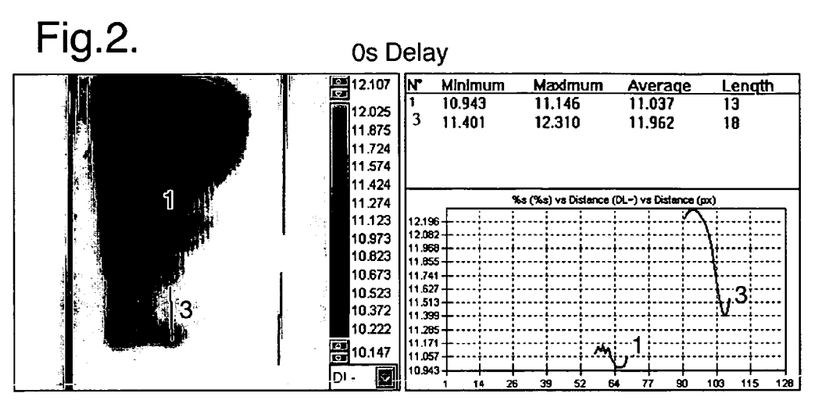
FIGS. 2 to 9 illustrate thermal images and graphical results produced in experimental trials of the apparatus.
Figure 3:
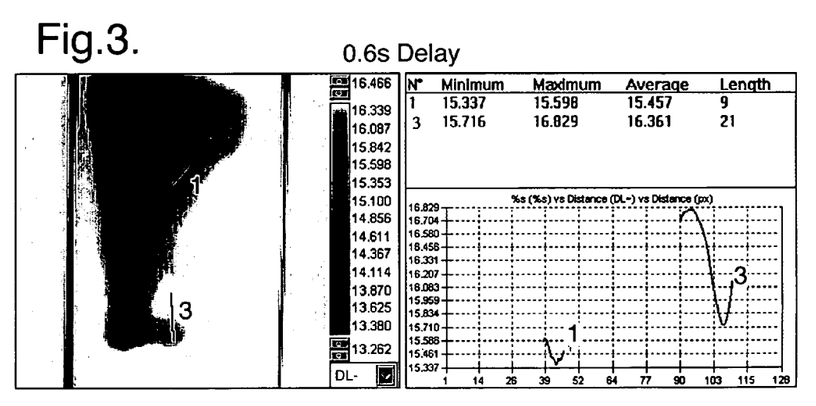
Figure 4:
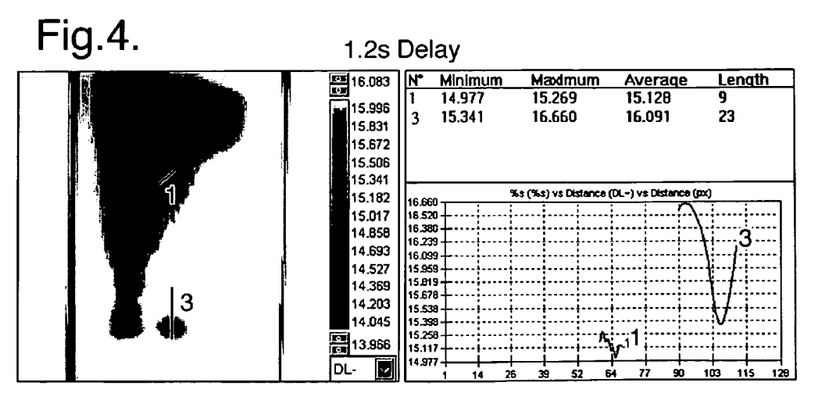
Figure 5:
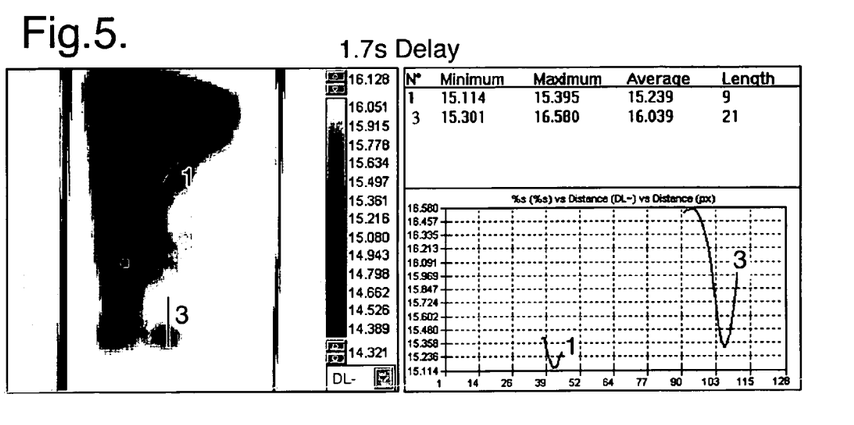
Figure 6:
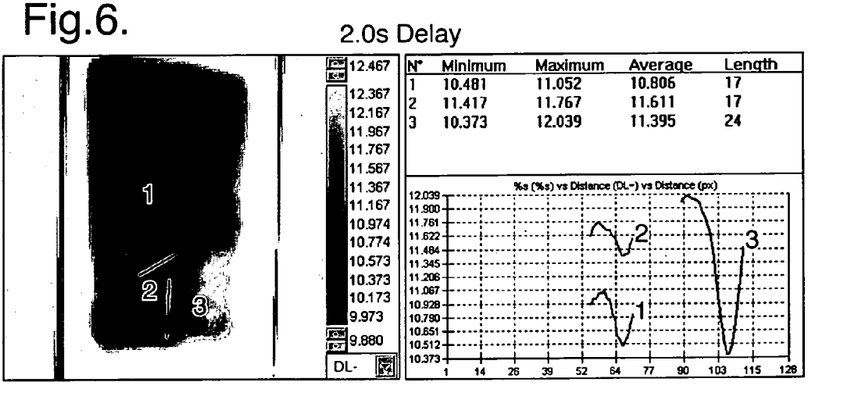
Figure 7:
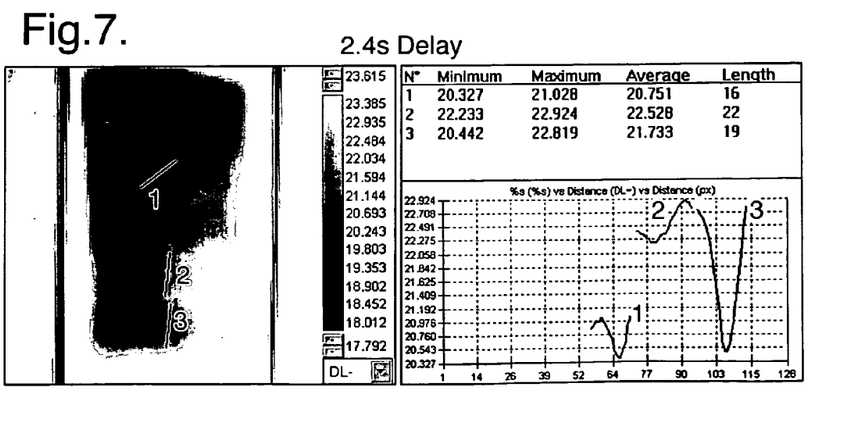
Figure 8:
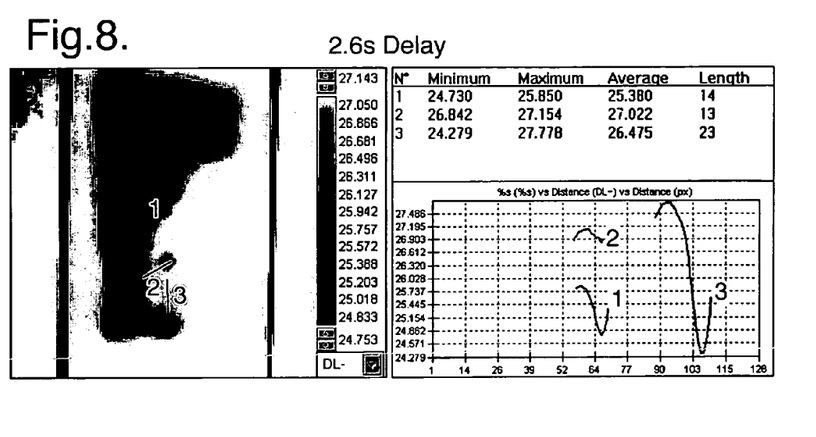
Figure 9:
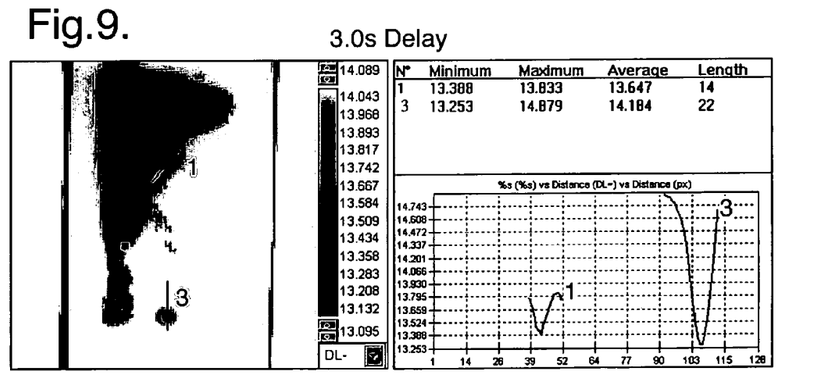

In FIG. 2, the amplitude image was taken with no delay (i.e. 0 seconds), whilst FIGS. 3 to 9 were taken with delays of 0.6 seconds, 1.2 seconds, 1.7 seconds, 2.0 seconds, 2.4 seconds, 2.6 seconds, and 3.0 seconds, respectively. The regions of the images marked 1, 2 and 3 refer to top, middle and bottom inclusion sites, respectively, on the images.

The PC of the thermography apparatus which was used to produce the Figures allows a line to be drawn between two points on the thermal image. The y-axes of the graphs on the right hand side of the Figures show the variation in digital level between the two end points of the lines, and the x-axes represents the positions of the lines drawn on the thermal image. Information regarding the minimum, maximum and average temperature between the end points of each line, as well as the line lengths is given above the graph.

It can be seen from the images that the PTFE sites become more visible as the delay time is increased. The middle inclusion (i.e. the one marked 2) only becomes visible for delay times between 2.0 and 2.6 seconds. The digital level (DL) for each PTFE inclusion site at a given Delay time is given in the table below:

| Delay Time and Digital Level for each PTFE Inclusion Site. | | | |
|---|---|---|---|
| Delay Time (S) | Inclusion 1 (DL) | Inclusion 2 (DL) | Inclusion 3 (DL) |
| 0.0 | 0.203 | — | 0.909 |
| 0.6 | 0.261 | — | 1.113 |
| 1.2 | 0.292 | — | 1.319 |
| 1.7 | 0.281 | — | 1.279 |
| 2.0 | 0.571 | 0.350 | 1.666 |
| 2.4 | 0.701 | 0.691 | 2.377 |

-continued

Delay Time and Digital Level for each PTFE Inclusion Site.

| Delay Time (S) | Inclusion 1 (DL) | Inclusion 2 (DL) | Inclusion 3 (DL) |
|---|---|---|---|
| 2.6 | 1.120 | 0.312 | 3.499 |
| 3.0 | 0.445 | — | 1.626 |

Figure 10:
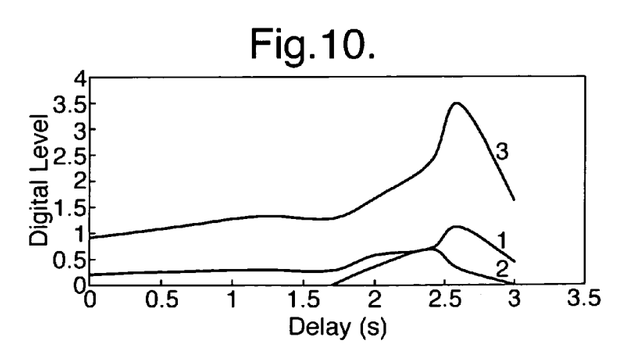
FIG. 10 is a graphical representation of the experimental results.

FIG. 10 represents the contents of the above table graphically. It can be seen that as the delay is increased, the PTFE inclusions become more visible as the amplitude of the digital level increases up to a delay of between 2.0 and 2.6s, after which the digital level decreases.

The three graph lines labelled 1, 2 and 3 correspond to the amplitude of the thermal signal from the respectively numbered inclusion which has been calculated from the charts on the right of FIGS. 2 to 9 by subtracting the minimum from the maximum digital level along the line profile drawn on the image to the left of the graph on FIGS. 2 to 9.

The image is, therefore, enhanced which significantly improves the overall capability of the material analysis apparatus. In the arrangement shown in FIG. 1, the camera receives heat pulses transmitted through the thickness of the sample. In an alternative embodiment shown in FIG. 11, a camera 206 receives heat pulses reflected from the thickness of the sample. Thus in FIG. 11 a halogen lamp 202 and an infra-red camera 206 are positioned facing the same side of a sample 201 of a material to be analysed, that is, otherwise the components are substantially identical and will not be described again.

Figure 12:
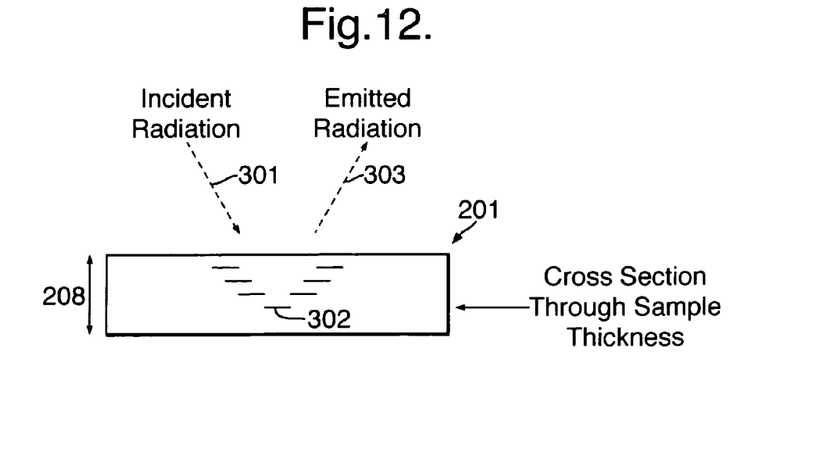
FIG. 12 illustrates schematically incident and emitted radiation which may be analysed by the embodiment of FIG. 11.

FIG. 12 illustrates schematically a magnified section through the thickness 208 of sample material 201. A heat pulse generated by the halogen lamp 202 diverts a beam and incident radiation 301 towards the surface of the sample 201 facing the lamp 202 and the camera 206. The radiation enters the surface of the sample and travels by means of lattice vibrations (phonons) within the material. If delaminations (e.g. represented by the lines 302) or imperfections are present within the material at a point through which the energy resulting from incident radiation 301 travels, then at least some of the energy is reflected and travels back up towards the surface where it is emitted in the form of thermal radiation. The resulting thermal radiation, represented by arrow 303, is transmitted from the surface of the sample to the lens of the camera 206.

It can be seen that a longer delay time is introduced between the incident and emitted radiation for delaminations located further from the surface of the sample. The signal delay box 207 is used to apply this delay time to produce clearer images of delaminations at different depths within the sample.

Figure 11:
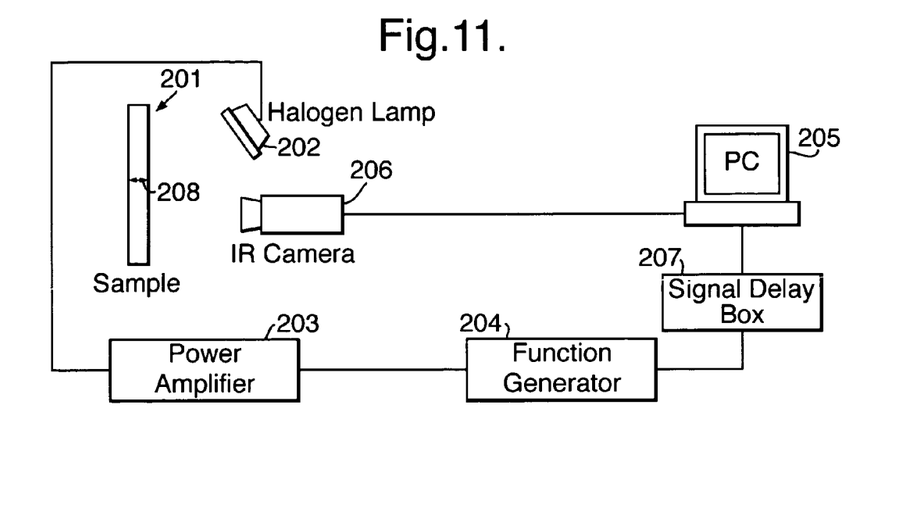
FIG. 11 illustrates schematically an alternative embodiment of the invention wherein a halogen lamp and an infra-red camera are positioned facing the same surface of a material sample.

Image enhancement of a delamination at a certain depth depends upon the amount of delay introduced between the function generator 204 and the PC 205 by the signal delay box 207. This technique effectively allows a "slicing" of a composite sample material to analyse delaminations at particular depths within it.

Compared with conventional thermographic imaging, the thermal image used by the present lock-in thermography imaging system is independent of external reflections, inhomogeneous illuminations, and emissivity, and so can be adapted for various inspection environments. The system is also reasonably portable.

The invention claimed is:

1. Material analysis apparatus for analyzing a material sample having two opposing sides separated by a thickness of material to be analyzed, said apparatus comprising:
   heat pulse emitting means for emitting a series of sinusoidally modulated heat pulses at one side of said material sample at a modulation frequency;
   thermal imaging means for viewing and capturing a series of thermal images of one of said two opposing sides of said sample at a capture rate greater than said modulation frequency; and
   delay means for introducing a delay between said emission of each one of said series of sinusoidally modulated heat pulses and capture of each of the respective series of thermal images at said viewed side, said delay sufficient to capture passage of said heat pulses rough at least a portion of said sample.

2. Apparatus according to claim 1, wherein said material sample is positionable between said heat pulse emitting means and said thermal imaging means.

3. Apparatus according to claim 2, wherein said series of pulses is emittable at a frequency approximately equal to 0.1 Hz and said delay is up to 3 seconds.

4. Apparatus according to claim 1, wherein said heat pulse emitting means and said thermal imaging means are positioned to face a common surface of said material sample.

5. Apparatus according to claim 4, wherein said delay is sufficient that said thermal image is captured when energy resulting from said emitted heat pulse is reflected from a selected point within a thickness of the sample to the surface of the sample.

6. Apparatus according to claim 5, wherein said selected point is represented by a distance measured from the surface of the sample.

7. Apparatus according to claim 1, wherein said thermal imaging means includes an infra-red camera.

8. Apparatus according to claim 7, further including means for storing digital data representing said image captured by said camera.

9. Apparatus according to claim 1, wherein said heat pulse emitting means includes:
   a halogen lamp; and
   means for switching said halogen lamp on and off at a predetermined frequency.

10. Apparatus according to claim 9, wherein the infra-red camera is configured to operate at a frequency of approximately 25 Hz such that it can capture approximately 25 thermal images per one second and the halogen lamp is switchable on and off at a frequency of approximately 0.1 Hz such that approximately 250 thermal images are capturable in a period of approximately 10 seconds.

11. Apparatus according to claim 10, wherein the 250 thermal images are usable to produce four averaged images.

12. Apparatus according to claim 11, configured to emit five said series of pulses and to capture five said series of thermal images such that twenty said averaged images are producable.

13. Apparatus according to claim 12, wherein the twenty averaged images are usable to produce a further averaged image.

14. Apparatus according to claim 9, wherein said delay means includes an operational amplifier circuit connected between said switching means and a personal computer connected to said thermal imaging means.

15. A method of analysing a sample to detect imperfections therein, said sample having two opposite sides separated by a thickness of material, said method comprising steps of:

emitting a series of sinusoidally modulated heat pulses towards one of said two sides of said sample at a frequency, and viewing and capturing a series of thermal images of one of said two sides of said sample at a capture rate frequency greater than heat pulse frequency, wherein a delay is introduced between said emission of said series of sinusoidally modulated heat pulses and capture of said respective series of thermal images, said delay sufficient to permit passage of at least a portion of energy from said heat pulses through a portion of said sample to said side of said sample from which said thermal image is viewed and captured.

16. Method according to claim 15, wherein said series of heat pulses are emitted at a frequency approximately equal to 0.1 Hz and a length of said delay is up to 3 seconds.

17. Method according to claim 15, further including a step of selecting a point within a thickness of the sample, wherein a length of the delay is sufficient that said series of thermal images are captured when energy resulting from said heat pulses is reflected from the selected point to said surface of the sample from which the thermal image is to be viewed and captured.

18. Method according to claim 16, wherein the series of thermal images are captured at a frequency of approximately 25 Hz such that approximately 250 thermal images are captured in a period of approximately 10 seconds.

19. Method according to claim 18, wherein the 250 thermal ages captured are used to produce four averaged images.

20. Method according to claim 19, wherein five said series of pulses are emitted and five said series of thermal images are captured such that 20 said averaged images are produced.

21. Method according to claim 20, wherein the 20 averaged images are used to produce a further averaged image.

22. Apparatus according to claim 1, wherein said time delay is variable.

23. Method according to claim 15, wherein said time delay is variable.

24. Material analysis apparatus, comprising:

heat emitting means for emitting a series of sinusoidally modulated heat pulses at one side of a material sample, at a predetermined modulation frequency;

thermal imaging means for capturing a series of thermal images of the same side of said sample at a capture rate having a frequency greater than said modulation frequency; and variable delay means for introducing a pre-adjusted delay between said emission of each one of said series of sinusoidally modulated heat pulses and capture of each of the respective series of thermal images, the value of the pre-adjusted delay being such that the energy of a heat pulse is reflected from a selected point within the thickness of the sample to the surface of the sample.

25. A method of analyzing a material sample to detect imperfections therein, comprising the steps of:

emitting a series of sinusoidally modulated heat pulses at a predetermined frequency towards one side of the material sample;

capturing a series of thermal images of the same side of said sample at a capture rate having a frequency greater than said predetermined frequency;

introducing a variable delay of pre-adjusted value between the emission of each one of said series of sinusoidally modulated pulses and capture of each of the respective series of thermal images, the value of the delay being adjusted such that the energy of a heat pulse is reflected from a selected point within the thickness of the sample to the surface of the sample.

* * * * *